United States Patent
Schmidt et al.

(10) Patent No.: US 6,319,190 B1
(45) Date of Patent: Nov. 20, 2001

(54) MEDICINAL RADIOACTIVE RUTHENIUM RADIATION SOURCES WITH HIGH DOSAGE RATE AND METHOD FOR PRODUCING THE SAME

(75) Inventors: Werner Schmidt, Berlin; Renate Freudenberger, Stuttgart; Michael Andrassy, Zepernick; Jürgen Ziegler, Berlin; Detlev Behrendt, Berlin; Andre Hess, Berlin, all of (DE)

(73) Assignee: Bebig Isotopentechnik und Umweltdiagnostik GmbH (DE)

( * ) Notice: Subject to any disclaimer, the term of this patent is extended or adjusted under 35 U.S.C. 154(b) by 0 days.

(21) Appl. No.: 09/424,895
(22) PCT Filed: Mar. 30, 1999
(86) PCT No.: PCT/EP99/02159
§ 371 Date: Feb. 14, 2000
§ 102(e) Date: Feb. 14, 2000
(87) PCT Pub. No.: WO99/50855
PCT Pub. Date: Oct. 7, 1999

(30) Foreign Application Priority Data

Mar. 31, 1998 (DE) .............................. 198 15 568

(51) Int. Cl.$^7$ .............................. A61N 5/00; A61N 36/00; B41M 5/20; C25D 5/10; C25D 5/12
(52) U.S. Cl. ................ 600/3; 600/7; 600/8; 205/50; 205/170; 205/176; 205/181; 205/191; 205/151
(58) Field of Search ................ 600/3, 7, 8; 205/159, 205/164, 167, 170, 176, 181, 191, 151, 50

(56) References Cited

FOREIGN PATENT DOCUMENTS

| | | |
|---|---|---|
| 2261944 | 7/1973 | (DE) . |
| 0018165 | 10/1980 | (EP) . |
| 1206612 | 2/1960 | (FR) . |
| 1520140 | 8/1978 | (GB) . |

OTHER PUBLICATIONS

G. Reddy et al.; Electrodeposition of Rutherium; Transactions of the Institute of Metal Finishing, 1969, vol. 47, pp. 187–193 no month available.

H. Drost et al.; Elektrolytische Abscheidung glänzender Rutheniumniederschläge aus Lösungen einfacher Rutheniumsalze; Isotopenpraxis, vol. 2, No. 4 1996; pp. 189–193 no month available.

Von A. F. Bogenschütz, et al.; Galvanische Abscheidung von Rutheniumschichten; Galvanotechnik 67, No. 2 (1976); pp. 98–105 no month available.

*Primary Examiner*—Edna Wong
(74) *Attorney, Agent, or Firm*—Norris, McLaughlin & Marcus PA

(57) ABSTRACT

The invention relates to radioactive ruthenium sources with a dosage rate of at least 1.5 Gy/min at a distance (water) of 2 mm, consisting of an activity carrier and an encapsulation of the carrier made of a material compatible with the human body. A multilayer system made of metals and/or alloys is galvanically applied on the carrier. At least two layers in said system are made of ruthenium 106 and inactive intermediate layers made of other metals or alloys are provided between the radioactive ruthenium layers. The activity carrier is encapsulated with a material compatible with the human body, for instance a metal or a plastic material. Encapsulation can be carried out by filing a capsule and subsequently sealing or galvanically depositing a top layer made, for instance of hard gold.

22 Claims, 2 Drawing Sheets

MEDICINAL RADIOACTIVE RUTHENIUM RADIATION SOURCES WITH HIGH DOSAGE RATE AND METHOD FOR PRODUCING THE SAME

BACKGROUND OF THE INVENTION

The invention relates to radioactive ruthenium radiation sources having a dose rate of at least 1.5 Gy/min at a distance of 2 mm (water), comprised of an activity carrier and an enclosure for said carrier made of a body-compatible material, the carrier having electrodeposited thereon a multilayer system of metals and/or alloys, wherein at least two layers consist of ruthenium-106, and wherein inactive intermediate layers of other metals or alloys are present between the radioactive ruthenium layers.

The activity carrier is enclosed in a body-compatible material such as metal or plastic. Enclosing the activity carrier can be performed by filling into a capsule and subsequent sealing, or by electrodepositing a cover layer made of e.g. hard gold.

The electrodeposition of non-radioactive ruthenium coatings on various substrates is well-known from the literature. A variety of electrolytes including most various additives have been described for this purpose. What is involved is the deposition of well-adhering coatings which are sufficiently thick and nevertheless glossing and free of cracks.

Thus, in the article by G. S. Reddy et al., "Electrodeposition of Ruthenium", in TIMF 47 (1969), pp. 187–193, for example, the anionic ruthenium complex $(NH_4)_3[Ru_2NCl_8(H_2O)_2]$ has been described as electrolyte, by means of which stable baths and glossing ruthenium coatings are obtained.

The DE-OS 22 61 944 concludes that coatings produced using such baths exhibit gloss only up to a thickness of about 2–3 $\mu$m, and that surface cracks will occur with increasing thickness. Therefore, this document suggests a modified electroplating bath, by means of which ruthenium layers 5 $\mu$m in thickness are said to be obtained. This bath likewise includes a complex ruthenium compound having the Ru—N—Ru nitrogen bridge (produced from the above-mentioned electrolyte), but is free of halogen, includes at least 1.5 g/l of sulfate ions, and has a pH value of 4 at maximum.

However, because the electrodeposition of ruthenium on copper, nickel or nickel-iron alloys does not proceed satisfactorily under acidic conditions for uses in electric engineering, and therefore, the substrate must first be coated with a thin layer of gold or another suitable material, some prior art documents have also described alkaline or neutral baths including complex ruthenium compounds having an Ru—N—Ru nitrogen bridge, e.g. in GB 1,520,140 of 1978 (alkaline) and in EP 0,018,165 of 1980 (addition of oxalic acid, pH value 7, diaphragm cell).

In context with the deposition of radioactive ruthenium layers, the French patent specification FR 1,206,612 (filed 1956) has been the first to be known from the literature. It essentially describes non-radioactive electrolytic depositions based on an electrolytic bath comprised of ruthenium (IV) chloride solution at 95–100° C. A coating of 4 mg/cm$^2$ is described, corresponding to a layer thickness of about 3 $\mu$m. Furthermore, it is noted in this written specification that a layer thickness of up to 8 mg/cm$^2$ would be possible when using this method. This would correspond to a layer thickness of about 6 $\mu$m. The problems with crack formation at layer thicknesses above 3 $\mu$m, which are well-known from the literature, have not been mentioned in this early document. Finally, this patent specification concludes that this method would also allow the production of radioactive sources but fails to demonstrate in which way such sources with sufficiently stable layers for medical uses could be obtained.

In contrast, a practical use of radioactive ruthenium is described in "Isotopenpraxis", Vol. 2, No. 4 (1966), pp. 189–193, wherein a deposition from highly diluted, inactive ruthenium(III) chloride solutions with addition of 30–70 $\mu$Ci of $^{106}$Ru as tracer has been performed.

However, it was found that the deposition described therein does not allow mechanically stable layers of significant thickness to be obtained, and that uniform distribution of activity on the preparations could only be achieved in excessively slow depositions. Such sources merely have limited usefulness for medical applications.

Marketed ruthenium radiation sources for ophthalmologic purposes are produced by electrolytic deposition of ruthenium from commercially available radioactive ruthenium (III) chloride solutions. The thin layers obtained thereby, having dose rates of from 0.1 to 0.5 Gy/min, are sufficient for using this radiation source as eye applicator in eye tumor treatment. However, these radiation sources are unsuitable in the treatment of vascular anomalies because they do not have the required dose rate due to the fact that thin layers can only be achieved.

SUMMARY OF THE INVENTION

It was therefore the object of the invention to provide radioactive ruthenium radiation sources for medical uses, which should have high dose rates and, despite the required thickness of the active ruthenium layer, have the required flexibility and geometry in order to be usable in the intravascular treatment of vascular anomalies. It was another object of the invention to devise methods of producing such sources.

According to the invention, said object is accomplished by means of radioactive ruthenium-106 radiation sources comprised of an activity carrier and an enclosure for said carrier made of a body-compatible material, the carrier having coated thereon a multilayer system of metals and/or alloys, wherein at least two layers consist of radioactive ruthenium, and wherein inactive intermediate layers of other metals or alloys are present between the radioactive ruthenium layers.

The radiation sources according to the invention have well-adhering ruthenium layers of the required thickness (and thus, the required dose rate) which remain free of visible cracks despite the bending stress typically occurring during use, e.g. in intravascular treatment of vascular anomalies.

The radiation sources of the invention are produced by electrolytic deposition of the multilayer system on a conductive carrier. According to the invention, the anionic ruthenium complex $[Ru_2NCl_8(H_2O)_2]^{3-}$ (RuNC), wherein the cations may be ammonium or potassium ions, is employed in the electroplating radioactive ruthenium bath. According to the invention, it was found particularly advantageous to add sulfopropylpyridine (PPS) to the electrolyte, preferably in amounts of from 1 to 10 mg per ml of electrolyte. The production of the RuNC electrolyte proceeds in a single step by hydrolyzing in excess amidosulfonic acid a ruthenium(III) chloride solution which, for purposes of the invention, contains at least 8 Ci/g ruthenium. Essentially, this production is known from the literature. Under the present active conditions, boiling at reflux is replaced by heating at about 90° C. The electrolyte thus obtained can be used without additional steps so that, according to the invention, the preparation of the electrolyte is performed directly in the electrolytic cell (cf., FIG. 1) developed for the process of the invention.

Gold, nickel, titanium or alloys thereof can be deposited as metals between the individual ruthenium layers. According to the invention, it is also possible to produce not all of the intermediate layers of the same metal but rather, use miscellaneous metals for the intermediate layers. In case the activity carrier is to be enclosed by a electrodeposited cover layer, gold may preferably be used for this purpose.

DETAILED DESCRIPTION OF THE INVENTION

Figure 1:
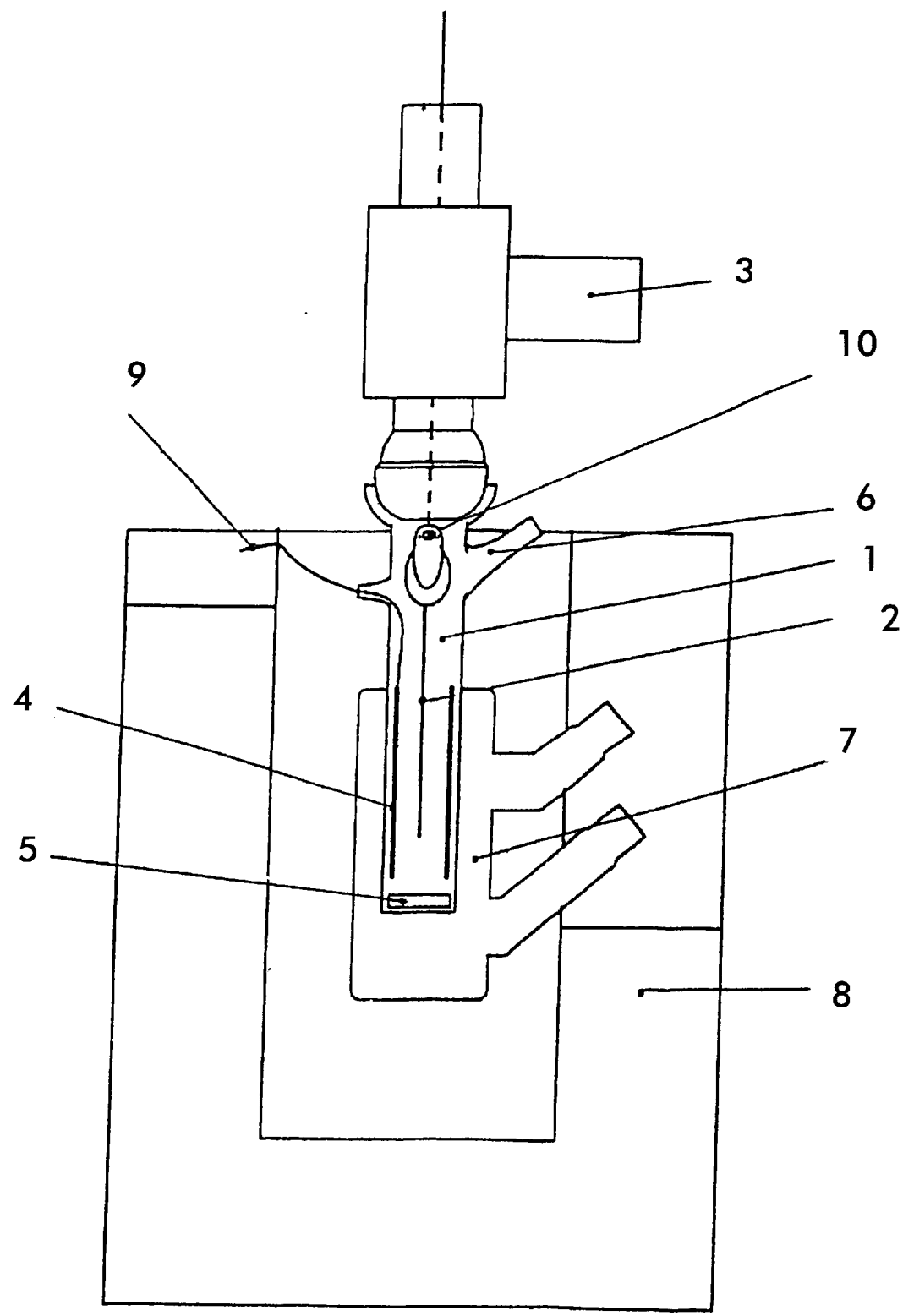
FIG. 1 illustrates a preferred embodiment of the electrolytic cell according to the invention.

In a preferred embodiment, the intermediate layers are also produced of gold where commercially available gold baths from the Degussa company may be used. Thus, it was found advantageous to select the Auruna® 311 electrolyte for the first gold layer on the carrier, which serves as an adhesion promoter between the carrier and the first ruthenium layer, and the Auruna® 533 electrolyte for the intermediate layers. If the radiation source is to be enclosed by a electrodeposited cover layer, the Auruna® 533 electrolyte is suitable in generating a hard gold layer in this case as well.

According to the invention, carriers made of brass, copper, alloyed steels, nickel, titanium, or alloys thereof, silver, gold, or platinum metals are possible as metallic carriers which simultaneously function as cathode. Preferably, nitinol or gold are used as carrier material. According to the invention, polymers modified at their surface, i.e., rendered electroconductive, may also be used as carriers. The carrier may have any desired shape or form. Likewise, it may be comprised of multiple carrier elements, each of which having the multilayer system. A tube or multiple tube-shaped elements, a single wire, or an array of multiple wires, a structured or non-structured foil, a mesh, a rotationally symmetrical molded body, or a sphere may be used as carrier. It is preferred to use a wire or a tube. In a particularly preferred embodiment, tube-shaped elements having a circular cross-section are used as carriers, which elements most preferably may consist of gold, the outer diameter at their ends being larger in size than that in the intermediate section (cf., FIG. 2a). In a preferred variant, the outer diameter of the tube-shaped elements is up to 0.6 mm at their ends, and up to 0.3 mm in the intermediate section. The length of the elements is 0.5–70 mm, depending on the desired use and the flexibility required. After the intermediate section has been coated according to the invention, preferably using multiple ruthenium layers and one cover layer, the tube-shaped elements now having a uniform outer diameter of e.g. 0.6 mm over their entire length (cf., FIG. 2b) are pushed on a flexible wire and secured against falling off at the ends thereof (e.g. by welding an end piece thereto). In their entirety, these tube-shaped elements "threaded" on the wire constitute the $^{106}$Ru radiation source (cf., FIG. 3). As a result of the individual free rotatability of each single element, particularly good flexibility of this radiation source is established.

The pretreatment of the carrier which is used is of essential importance for the adherence of the multilayered coating according to the invention. The carrier has to be degreased, and oxide layers possibly present and—should the occasion arise—tightly adhering particles have to be removed. When using nitinol as carrier, final pickling using a mixture of hydrofluoric acid and hydrochloric acid has proven advantageous. In a preferred embodiment, a gold layer as adhesion promoter is coated as first layer on the nitinol carriers.

If the carriers are made of gold, previous gilding can obviously be omitted. If tube-shaped elements as described above are to be coated, the sections at their ends which should remain free have to be coated with a masking lacquer.

The inventive electrolytic deposition of the ruthenium layers proceeds under observance of the following operating parameters: The ruthenium concentration at the beginning of the electrolysis typically is 5 g/l and may drop down to 0.2 g/l as a result of ruthenium depletion. The temperature should be between 60 and 75° C., preferably 70° C., and the pH value must be maintained between 1.3 and 1.8. Ruthenium concentration and pH value are controlled and adjusted at regular intervals.

According to the invention, ruthenium-106 radiation sources are provided in this way which have sufficiently thick, well-adhering, crack-free, homogeneous, and flexible radioactive ruthenium layers.

In order to achieve a layer thickness of >7 $\mu$m, coating of metallic intermediate layers was found to be indispensable. Only in this way the required mechanical stability is achieved, which is necessary for use as a radioactive radiation source of a specific geometry, and only in this way the coating produced using the process according to the invention remains free of visible cracks even on flexible carriers, such as a wire, despite the bending stress typically occurring in radiation sources during use.

According to the invention, radioactive ruthenium layers having a thickness of up to 5 $\mu$m are achieved when adjusting current densities of between 0.25 and 0.35 A/dm$^2$. By multiple coating involving metallic intermediate layers, ruthenium-106 overall layer thicknesses of up to 30 $\mu$m are achieved, where the overall layer thickness is understood to be the sum of all radioactive ruthenium layers. The ruthenium radiation sources produced from these multi-coated ruthenium activity carriers have a dose rate of at least 1.5 and up to 15 Gy per minute at a distance of 2 mm (in water).

According to the invention, a special electrolytic cell for the preparation of the electrolyte and the subsequent electrolytic deposition of ruthenium has been developed. The electrolytic cell preferably employed according to the invention is comprised of a vessel 1 having a double-jacket 7 for heating. With respect to its dimensions, the electrolytic vessel 1 must comply with the demand for minimum operating volume. Preferably, the operating volume should not exceed 5 ml. Moreover, the electrolytic vessel 1 for preparing and adjusting the electrolyte must be suitable in such a fashion that addition of liquids through an opening 10 and stirring of the electrolyte by means of a stirrer 5 is possible. Also, the cathode 2 should be capable of immersing into the electrolyte in a positioned fashion according to the desired active length. According to the invention, the electrolytic cell has been designed in such a way that cathode 2 is joined to a means for opening the operating space 3. In a preferred arrangement, the anode 4 coaxially surrounds the cathode 2. Above the liquid level of the electrolyte, the electrolytic vessel 1 comprises an element 6 for withdrawing gases and vapors, allowing a slight vacuum to be applied permanently.

EMBODIMENTS

EXAMPLE 1

Electrolytic production of radioactive ruthenium layers wherein a nitinol wire 0.3–0.5 mm in diameter is used, and the intermediate layers as well as the cover layer are made of gold.

1. Pretreatment

Processing sequence of pretreatment (including intermediate rinsing steps):
1. Ultrasonic degreasing [40 g/l, 60° C., 2 min, Slotoclean AK 1190 (Schlötter company)]
2. Cathodic degreasing [100 g/l, RT, 0.3 min, Slotoclean EL-KG (Schlötter company)]
3. Anodic activation (sulfuric acid 5%, RT, 0.25 min)
4. Pickling [HF/HCl (4%, 18%), RT, 0.25 min]
(optionally repeat 3. and 4. periodically)

2. Intermediate layers

Previous gilding is used to promote adhesion between the substrate and the Ru layer. The commercial electrolyte Auruna® 311 is selected as primary gold. The previous acid activation is already provided by pickling. Gold is also suitable as intermediate layer between the Ru depositions, to which end the Auruna® 533 electrolyte is selected. Preactivation is effected by pickling with sulfuric acid (5%, RT, 0.5 min). Both electrolytes are cyanogold complexes from the Degussa company.

Process parameters

Primary gold: Auruna® 311 (Degussa company, 2 g/l, RT, 10 min, 2 A/dm$^2$)

Intermediate layers

Auruna® 533 (Degussa company, 8 g/l, 35° C., 7 min, 1 A/dM$^2$)

3. Ru deposition

The Ru complex RuNC is used as electrolyte. Preparation is effected in advance, directly in the specially developed electrolytic cell. The electrolyte is modified by adding PPS (sulfopropylpyridine, 3 g/l, Raschig company).

The operating parameters of the Ru electrolysis are:
Ru concentration range: 4.8–0.2 g Ru per 1
Current density: 0.25–0.35 A/dm$^2$
Temperature: 70° C.
pH value: 1.3–1.8
Agitation of bath: none
Electrolyte volume (5 ml max.)

4. Cover layer

For those cases of use where a cover layer is required, such a layer may likewise be produced of hard gold (in analogy to the intermediate layers using Auruna® 533).

EXAMPLE 2

Production of a radioactive ruthenium radiation source by electrolytic formation of radioactive ruthenium layers on a conductive carrier in such a way that a nitinol tube or wire having an outer diameter of 0.2–0.6 mm is coated over a length of 0.5–7 cm, and intermediate layers as well as a cover layer of gold are used.
1. Pretreatment as in Example 1
2. Intermediate layers as in Example 1
3. Ru deposition as in Example 1
4. Cover layer Regarding the production of an enclosed radiation source, the cover layer in its quality parameters must ensure absence of pores to prevent wash-our of radioactive Ru, absence of cracks under mechanical stress typically occurring during use, as well as wear resistance against abrasion on High Density Polyethylene (HDPE). Such a cover layer can be made of hard gold (see Example 1).

EXAMPLE 3

Production of a radioactive ruthenium radiation source using tube-shaped elements having enlarged outer diameter at their ends.

Tube-shaped parts having sectionally varying outer diameters are employed as carriers (overall length: 1.3 mm, diameter at the ends: 0.3 mm, diameter in the intermediate section: 0.2 mm, length of intermediate section: 1 mm).

The elements consist of gold and are to be ruthenium-coated on their thin intermediate sections only. This object is accomplished by covering those sections which have to remain free with a non-conductive masking lacquer.

The pretreatment of the carriers is performed as described in Example 1, omitting step 4. Previous gilding is not necessary. Ruthenium deposition is effected as in Example 1. The cover layer is coated as described in Example 1. As the cover layer is to be coated on the masked tube sections as well, the masking lacquer is removed therefrom by dissolving in acetone.

The tube-shaped elements of uniform length produced in this way are pushed on a wire and secured against falling off at the ends thereof (e.g. by welding an end piece thereto).

Depending on the type of use, varying numbers of bodies may be threaded. As a result of the individual free rotatability of the single elements, flexibility of the overall arrangement is established.

EXAMPLE 4

Production of a radioactive radiation source designed for special mechanical stress, using tube-shaped elements having enlarged outer diameter at their ends.

Tube-shaped parts having sectionally varying outer diameters are employed as carriers (overall length: 1.3 mm, diameter at the ends: 0.28 mm, diameter in the intermediate section: 0.2 mm, length of intermediate section: 1 mm). The elements consist of gold or titanium and are to be ruthenium-coated on their thin intermediate sections only. This object is accomplished by covering those sections which have to remain free with a non-conductive masking lacquer.

The pretreatment of the carriers is performed as described in Example 1. Ruthenium deposition is effected as in Example 1. Subsequently, the masking lacquer is removed by dissolving in acetone.

However, the gold cover layer is not coated. Instead, the tube-shaped parts are inserted in a larger tube of the same material. At the ends thereof, the uncoated edge of the activity carrier (outer diameter: 0.28 mm) is welded with the sealing tube.

The tube-shaped elements of uniform length now being encapsulated are pushed on a wire and fixed at both ends. Depending on the type of use, varying numbers of bodies may be threaded. As a result of the individual free rotatability of the single bodies, flexibility of the overall arrangement is established. Owing to the encapsulation of the single bodies, higher stability and, in particular, higher abrasion resistance is achieved.

INDEX OF REFERENCE NUMBERS

FIG. 1

1 Electrolytic vessel
2 Cathode
3 Means for opening the operating space

Figure 2:
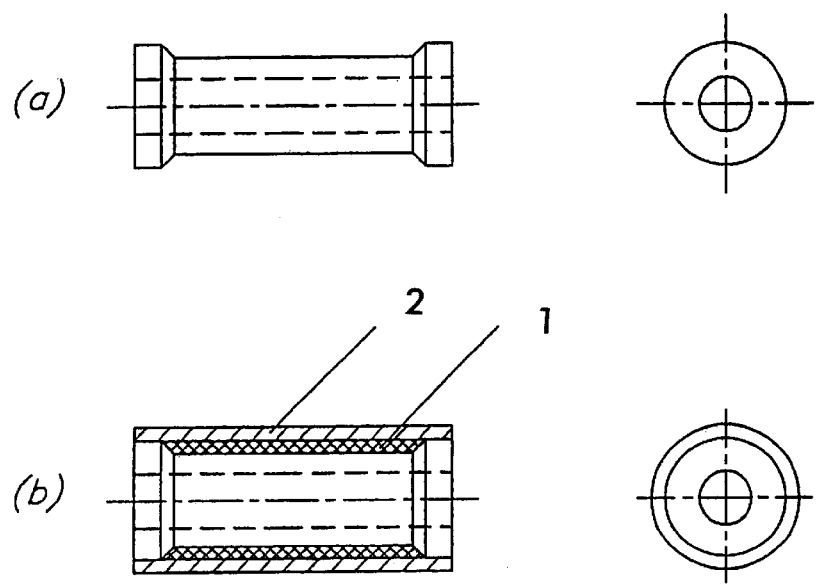
FIG. 2 illustrates a) non-coated and b) coated tube-shaped carrier elements employed in a preferred embodiment.
Figure 3:
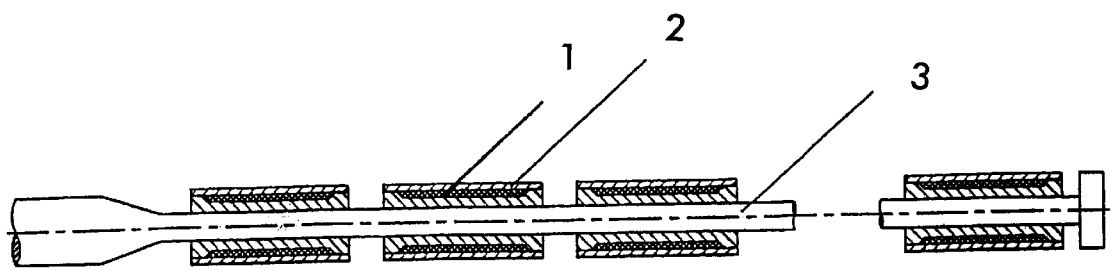
FIG. 3 illustrates the coated tube-shaped elements "threaded" on a wire which, in their entirety, represent the ruthenium-106 radiation source.

4 Anode
5 Magnetic stirrer
6 Element for air withdrawal
7 Double jacket
8 Lead screening
9 Anode contacts
10 opening for addition of liquids
FIG. 2
1 Multiple coating including at least two Ru-106 layers
2 Enclosure
FIG. 3
1 Multiple coating including at least two Ru-106 layers
2 Enclosure
3 Wire

What is claimed is:

1. A medical radioactive ruthenium radiation source having a dose rate of at least 1.5 Gy/min at a distance of 2 mm in water, comprising an activity carrier and an enclosure for said carrier made of a body-compatible material, the carrier having coated thereon a multilayer system of metals and/or alloys, wherein at least two layers consist of radioactive ruthenium, and wherein inactive intermediate layers of other metals or alloys are present between the radioactive ruthenium layers.

2. The radiation source according to claim 1, wherein the carrier material is selected from the group consisting of brass, copper, alloyed steel, nickel, titanium, or alloys thereof, silver, gold, and a platinum metal.

3. The radiation source according to claim 2, wherein the carrier material is nitinol or gold.

4. The radiation source according to claim 1, wherein the inactive inter mediate layers of the multilayer system is selected from the group consisting of gold, nickel, titanium, and alloys thereof.

5. The radiation source according to claim 4, wherein the inactive intermediate layers of the multilayer system are of gold.

6. The radiation source according to claim 1, wherein the overall layer thickness of the radioactive ruthenium layer is at least 7 $\mu$m, where the overall layer thickness is the sum of all radioactive ruthenium layers.

7. The radiation source according to claim 1, wherein the activity carrier is comprised of multiple carrier elements, each one having the multilayer system according to claim 1.

8. The radiation source according to claim 1, wherein the activity carrier is a tube or an array of multiple tube-shaped elements, a single wire, or an array of multiple wires, a structured or non-structured foil, a mesh, a rotationally symmetrical molded body, or a sphere.

9. The radiation source according to claim 1, wherein the activity carrier represents an array of multiple tube-shaped elements of circular cross-section, which elements are pushed on a wire and fixed at the ends thereof.

10. The radiation source according to claim 1, wherein the enclosure for the carrier is a metal layer electrodeposited on the multilayer system.

11. The radiation source according to claim 10, wherein the enclosure is gold.

12. The radiation source according to claim 1, wherein the enclosure for the carrier is a capsule made of metal or plastic.

13. The radiation source according to claim 12, wherein the enclosure for the carrier has the shape of a tube.

14. A method of producing medical radioactive ruthenium radiation sources by electrolytic deposition of radioactive ruthenium on a conductive carrier, wherein a multilayer system of metals and/or alloys is electrodeposited on the conductive carrier, wherein at least two of said layers are produced of radioactive ruthenium, and inactive intermediate layers of other metals or alloys are coated between the radioactive ruthenium layers, and the activity carrier thus obtained is enclosed by a body-compatible material.

15. The method according to claim 14, wherein the multilayer system includes an electroplating bath for the deposition of a layer consisting of radioactive ruthenium, wherein the electroplating bath is based on an electrolyte including the anionic ruthenium complex $[Ru_2NCl_8(H_2O)_2]^{-}$ which is produced from a radioactive ruthenium (III) chloride solution by hydrolysis without any intermediate steps with addition of excess amidosulfonic acid.

16. The method according to claim 15, wherein the ruthenium electroplating bath includes sulfopropylpyridine (PPS) as an additive.

17. The method according to claim 15, wherein electrolyte production and ruthenium electrodeposition are effected in the same electrolytic cell.

18. The method according to claim 17, wherein the electrolytic cell is comprised of a vessel having a double-jacket for heating, the cathode of which is joined to a means for opening the operating space, the anode of which coaxially surrounds the cathode, and the vessel of which, above the liquid level of the electrolyte, comprises an element for withdrawing gases and vapors and an opening for addition of liquids.

19. The method according to claim 14, wherein gold from a conventional gold electroplating bath containing a cyanogold complex as electrolyte is deposited as the metal for the inactive intermediate layers not containing any radioactive ruthenium.

20. The method according to claim 14, wherein brass, copper, alloyed steels, nickel, titanium, or alloys thereof, silver, gold or platinum metals which simultaneously form the cathode are used as carrier material.

21. The method according to claim 14, wherein tube-shaped elements having a circular cross-section are used as carriers, the outer diameter at each end of which being larger in size than that in the intermediate section thereof, and which elements, following coating of the intermediate section, are pushed on a wire and fixed at the ends thereof.

22. The method according to claim 21, wherein said tube-shaped elements have an outer diameter of up to 0.6 mm at their ends and an outer diameter of up to 0.3 mm in the intermediate section to be coated.

* * * * *